United States Patent [19]
Browne

[11] 4,098,116
[45] Jul. 4, 1978

[54] LIQUID FLOW AND VOLUME RECORDING APPARATUS AND METHOD

[75] Inventor: Lawrence T. Browne, Santa Barbara, Calif.

[73] Assignee: Browne Engineering Corporation, Santa Barbara, Calif.

[21] Appl. No.: 741,795

[22] Filed: Nov. 15, 1976

[51] Int. Cl.² .................. G01G 11/06; G01G 3/02
[52] U.S. Cl. ............................. 73/194 M; 177/16
[58] Field of Search ............... 73/194 R, 194 M, 228; 177/16

[56] References Cited
U.S. PATENT DOCUMENTS 1,883,017  10/1932  Sholtz .......................... 177/16 X 3,269,181  8/1966  Seay ............................ 73/194 M X

FOREIGN PATENT DOCUMENTS 430,281  11/1974  U.S.S.R. ...................... 73/194 M

*Primary Examiner*—James J. Gill
*Attorney, Agent, or Firm*—Donald D. Mon

[57] ABSTRACT

Means for measuring and recording the instantaneous rate of flow of a liquid such as a stream of urine, and an accumulated volume of said fluid. The rate is measured by causing it to flow along a measured sloping channel supported by a deflectable beam and gauging the deflection of the beam. The total flow is measured by collecting the liquid in a container supported and gauged in the same way. The system can be entirely gas-operated.

10 Claims, 5 Drawing Figures

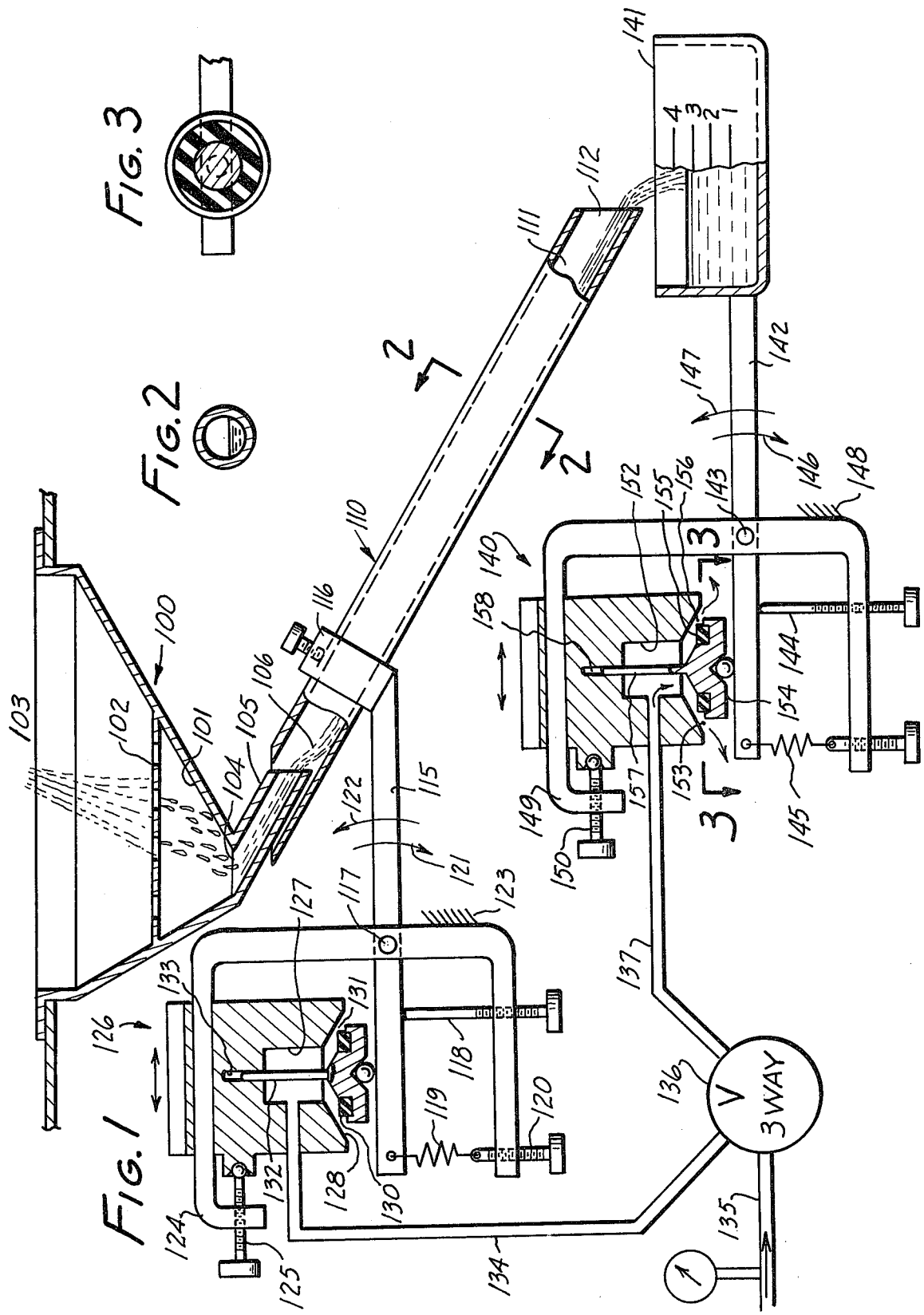

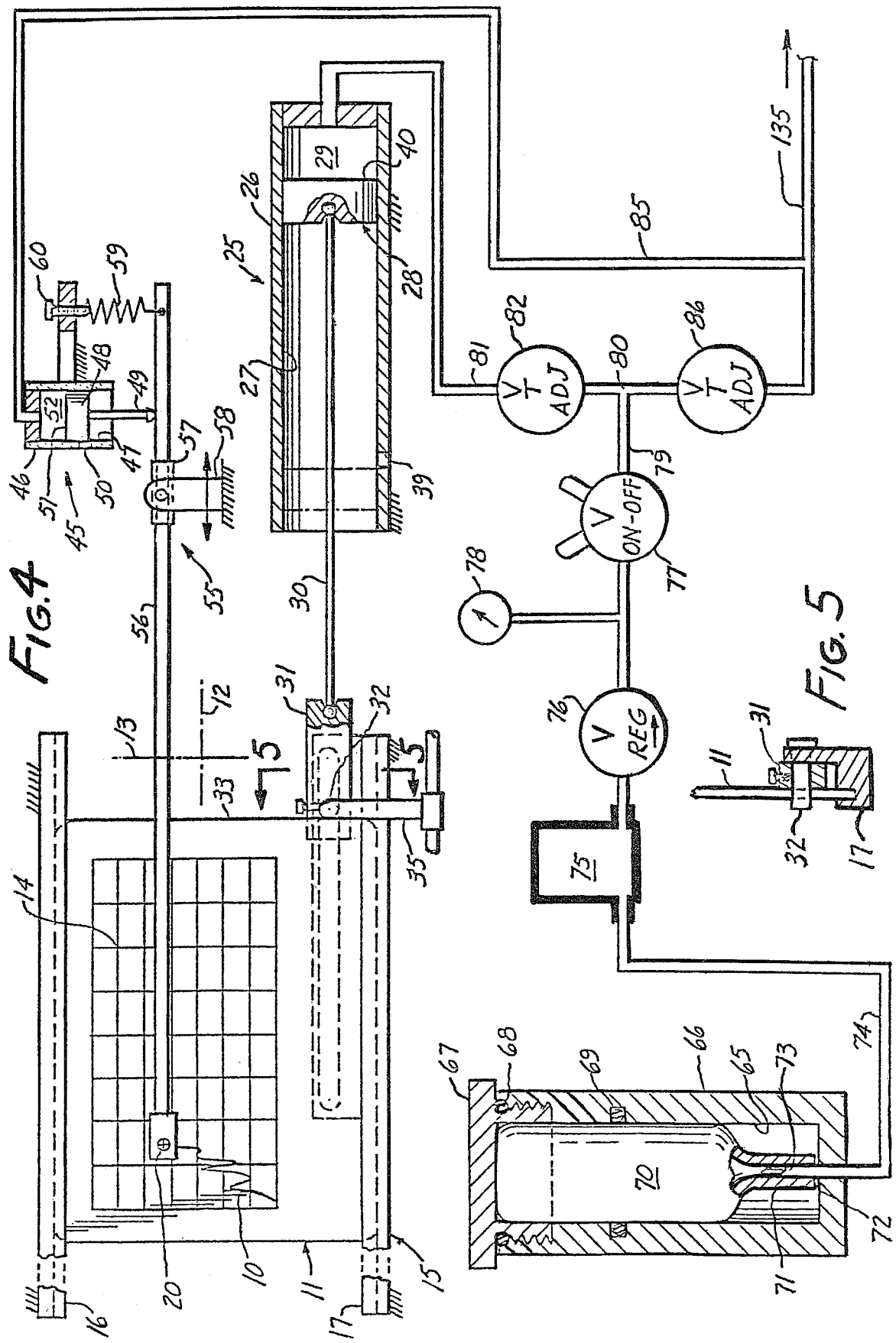

LIQUID FLOW AND VOLUME RECORDING APPARATUS AND METHOD

This invention relates to a means for measuring and, if desired recording, the instantaneous rate of flow of a stream of liquid and/or its accumulated volume over a period of time.

In the medical field of urology, it is useful to determine the pattern of urination of a patient. This determination requires a knowledge of the rate of flow of urine at a given time in the course of a urination cycle. Musculature and physiological restriction problems can be recognized from various patterns. It is also useful to measure the total volume.

Diagnosis of this type is most conveniently done in the physician's office. It needs to be carried out with a minimum of supervision, to avoid distraction which could affect the cycle. Accordingly, it is an object of this invention to provide an apparatus to receive a flow of liquid such as urine, which is self-powered and requires no supervision, for measuring and, if desired, also for recording the instantaneous rate of flow of urine.

Apparatus according to this invention includes sloped channel means having an outlet and a known length. The amount of liquid in the channel means at any time is a function of the rate of liquid flow through the channel. Deflectable beam means supports the channel means, the weight of the channel and of liquid in the channel tending to deflect the beam in a first direction. Bias means tends to deflect the beam in a second, reverse, direction. Gauge means is disposed so as to measure the deflection of the beam, and thereby to determine the weight of liquid in the channel. According to a preferred form of the invention, the gauging means comprises a variable orifice whose size is a function of the weight of liquid in the channel means, and which provides means for generating a pressure which is proportional to the instantaneous rate of flow.

As an optional feature of the invention, a receptacle is placed on the beam to accumulate the liquid, and the gauging means then measures accumulated volume.

The above and other features of this invention will be fully understood from the following detailed description and the accompanying drawings, in which:

FIG. 1 is a side elevation, partly in schematic notation and partly in axial cutaway cross-section;

FIG. 2 is a cross-section taken at line 2—2 of FIG. 1;

FIG. 3 is a cross-section taken at line 3—3 of FIG. 1; and

FIGS. 4 and 5 show a system useful for supplying fluid to the gauging means and for reading out and recording the measured data.

A trap 100 is shown in FIG. 1 which has a funnel-shaped bottom 101 located beneath a screen 102. A stream 103 of liquid, such as urine, collects at the bottom 101 and leaves through an opening 104 from which it flows down a sloped spout 105. The sloped spout discharges its stream 106 gently near the upper end of sloped channel means 110 which has a channel 111 with an outlet 112 at its lower end. The spout does not contact the channel means, and is both close to it, and nearly parallel to it in the normal range of liquid flow.

The channel means is mounted on a deflectable beam 115. A clamp 116 holds it to the beam. The beam is pivotally mounted to a pivot pin 117 for bi-directional rotation around the pivot. "Rotation" is treated as one type of "deflection".

An adjustable threaded limit stop 118 limits the counter-clockwise rotation of the beam. An adjustable tension spring 119 on a threaded stem 120 tends to rotate the beam counter-clockwise and constitutes a bias means. The beam is deflectable in a first, clockwise, direction 121 in response to weight of fluid in the channel means, and in a second, opposite, counter-clockwise direction 122 in response to the force exerted by the tension spring. The spring has a spring constant. The deflection of the beam is therefore uniquely related to the weight of the urine in the channel means.

The apparatus is supported on a base 123. The base includes a flange 124, through which an adjustment lead screw 125 is threaded so as to move gauging means 126 to the right or left in FIG. 1, toward and away from pivot pin 117. This provides for a fine adjustment of gauging response to the weight of the urine in the channel means.

Gauging means 126 includes a chamber 127 with a conical opening 128 at its bottom. An orifice member is located in the opening. It rests atop the beam. It can close the opening by means of a peripheral seal 130 carried by the orifice member. When the orifice member moves away from the opening, it forms an air gauge orifice 131 whose size is determined by the weight of the liquid in the channel means. There is a unique beam deflection for every weight, as determined by the spring constant. The orifice member is guided by a stem 132 in a counterbore 133 in the top of the chamber.

A gauging conduit 134 supplies fluid under pressure to the chamber. This is derived from a delivery conduit 135 through a selector valve 136 which can be set to supply fluid either to gauging conduit 134 or to gauging conduit 137.

A total-volume measurement device includes gauging means 140 similar to the gauging means already described. A receptacle 141 is supported at the end of a pivoted beam 142. In turn, the beam is deflectably mounted by a pivot pin 143. An adjustable threaded limit stop 144 limits the counter-clockwise deflection of the beam. A bias tension spring 145 tends to force the left-hand end of the beam toward the limit stop. The beam is deflectable in a first, clockwise, direction 146 or in a second, opposite, counter-clockwise, direction 147.

A base 148 has a flange 149 which supports an adjustable lead screw 150 to move the second gauging means toward or away from the pivot. Second gauging conduit 137 enters chamber 152 of the second gauging means. There is an opening 153 at the bottom of the chamber in which there is an orifice member 154 with a peripheral seal 155 above it to form an air gauge orifice 156. A stem 157 is guided in a counterbore 158 in the top of the chamber.

The system in operation measures the backpressure which arises in the respective gauging line as a function of the deflection of the beam in the first direction in opposition to the bias of the spring. This is a common air gauging practice. Persons skilled in the art of air gauging will recognize that the beam, instead of being pivoted, could instead be cantilevered, and be inherently springing or self biased. The bias means in that arrangement is the inherent springiness of the beam. Also, the bias means and the receptacle could be located on the same side of the pivot pin. All of these arrangements are within the scope of the invention.

In operation the supply line supplies fluid at a regulated pressure. This fluid is discharged through the variable gauging orifice. The pressure in the gauging conduit upstream from the variable orifice reflects the amount of opening of the orifice. The more liquid there is, the more closed is the orifice and the closer to supply pressure will the pressure in the chamber be. Conversely, the less liquid there is, the lower is the pressure in the chamber.

The best practice is to place an orifice (throttle) downstream from a pump or regulator or other source of pressure, so that the pressure variation caused by changes in the variable orifice are somewhat more sensitive and precise. This is a design feature which will be recognized by persons skilled in the art of air gauging. In any event the deflection of the beam will be directly reflected by the amount of opening of the orifice, and a resulting change in the pressure in the chamber (or other location between the source and the variable orifice). It is only necessary to measure this pressure to provide a direct indication of the weight of urine in the channel means. A gauge could be connected to the chamber to provide a visual read-out.

The operation of the second gauging means is the same as that of the first gauging means, except that instead of measuring a transient value which can increase and decrease, it measures an accumulated weight which continuously increases. In both cases, however, the resulting pressure (sometimes called "backpressure") appears at a location upstream from the variable orifice.

A useful system for supplying gas to the system to operate the gauging means and means to measure and record the weights is shown in FIGS. 4 and 5.

The ultimate objective of this part of the system is to draw a graph line 10 on a chart 11 recording a timebase and either the simultaneous rate or the accumulated volume at that time. The graph has a first axis 12 and a second axis 13. In FIG. 1, first axis 12 is for the timebase. This base is only approximately correct, because the rate of movement on its axis will be slightly affected by the rate and volume, but it is close enough. The second axis is for the rate or weight. A typical rectangular coordinate system 14 is printed on the chart, divided into appropriate units.

Chart support means 15 comprises a pair of tracks 16, 17. The chart, or a device supporting the chart, travels to the right or left along first axis 12. Marker means 20, such as a recording pen, is brought against the chart to draw the graph line.

A first axis motor 25 comprises a piston-cylinder assembly which includes a cylinder 26 having a circularly cylindrical bore 27 within which a circularly cylindrical piston 28 is reciprocably fitted. The piston and the wall of bore 27 make a close, fluid-sealing sliding fit with one another. Fluid pressure in chamber 29 tends to enlarge chamber 29 and move piston 28 to the left. Connecting rod 30 is connected to piston 28 and to a slide mamber 31 which is slidably mounted to track 17.

Slide member 31 carries a stud 32 which abuts against the right-hand edge 33 of chart 11. The connecting rod, slide member, and stud constitute means whereby the first axis drive motor is enabled to move the chart to the left in FIG. 1 relative to the support means.

A vent port in the form of a groove 39 is cut through the wall of cylinder 26. When the right-hand face 40 of the piston passes the right-hand edge of vent groove 39, pressure will be dumped from chamber 29, and the chart movement will stop. This will also stop delivery of fluid, as will more fully be discussed below.

In operation, the first axis motor is unidirectionally driven. It can be restored to a starting position by manually pushing the chart or the link 35 to the right in FIG. 4 while chamber 29 is connected to atmosphere.

Second axis motor 45 also comprises a piston-cylinder assembly. It includes a cylinder 46 having a bore 47 in which a piston 48 makes a close, fluid-sealing, sliding fit. It can reciprocate axially in the cylinder and includes a push rod 49 which projects beyond the open end of the cylinder. A vent port in the form of a groove 50 is cut through the wall of the cylinder so that when face 51 of the piston passes the edge of the groove, pressure will be vented to atmosphere from chamber 52. This constitutes a limit for the maximum pressure which can be applied to the second motor and to the gauging means.

Marker support means 55 comprises a pivoted arm 56. It may conveniently be supported in a pivoted sleeve 57. Sleeve 57 is pivoted to a block 58. The location of the block along the length of the pivoted arm is adjustable. This adjusts the range of the left-hand end of the pivoted arm to which the marker is attached. This provides for a multi-range read-out, because the same deflection of the end of the arm can be made to read out different selected pressures.

The push rod 49 presses downwardly against the right-hand portion of the arm. Its downward pressure is opposed by a bias spring 59. Spring 59 is a tension spring connected to an attachment 60 that is fixed relative to the frame of the machine or relative to the cylinder 46. It is also connected to the right-hand portion of the pivoted arm. Attachment 60 is a screw which can be turned to adjust the tension of the bias spring. Therefore, the position of the arm will also be determined by the interaction between bias spring 59 and the pressure in chamber 52. Tension on the spring can also be adjusted to determine the pressure range, and will more usually be the means to secure this objective.

The rate or weight will be recorded as a function of the vertical position of the marker on the chart, which is set by the second motor. The timebase, which is really a measure means of the accumulated total volume of gas passed from the start of the procedure to the moment of recording will be determined by the position of the chart relative to its support as set by the first motor. The term "motor" is used in this specification in its broadest sense. Motive means other than piston-cylinder assemblies can be used instead, positive-displacement vane-type and gear type rotary motors, for example. Piston-cylinder assemblies are the least complicated.

Because the pressures utilized in this system are relatively low, and the pressure differentials measured are small portions of it, it is important to have as little frictional loss in the system as possible. For example, a delivered pressure will often approximate 8 psi, and backpressure differentials to be measured will be on the order of 0.13 psi. A suitable low friction motor can be made from an accurately cylindrical and smooth glass cylinder, and an accurately cylindrical and smooth graphite piston. These make a very satisfactory fluid seal with one another, and yet have only negligible sliding friction losses between them.

The foregoing describes the mechanical features of the invention. The fluid flow features will now be described.

A receiver 65 comprises a strong-walled vessel 66 having a removable pressure-tight cap 67 with seals 68, 69. It receives a typical carbon dioxide pressure cartridge 70. Such cartridges have a neck 71 with a tip 72 which is penetrable by a needle 73 to release the gas. It is usual for the initial pressure in such a gas cartridge to be on the order of 900 psi. When released, the gas flows through a pressure line 74 to a tank 75 which, although shown smaller on the drawings for convenience in illustration, will usually be about 9 to 10 times the volume of the cartridge, whereby to reduce the maximum pressure in the system to about 100 psi.

A pressure regulator valve 76 receives gas from the tank and supplies it at adjustably regulated pressure to an off-on valve 77. This is usually about 8 psi. A flow rate gauge 78 is teed into line 79 downstream from the pressure regulator to indicate the approximate gas flow rate. It may simply be a pressure gauge calibrated to indicate rate. The off-on valve 77, when open, delivers fluid at the predetermined regulated pressure. The apparatus upstream from, and including valve 77, is sometimes referred to as a "pressure-regulated fluid supply means". It delivers fluid to a tee 80.

A first axis conduit 80 connects the pressure regulated fluid supply means to chamber 29 of first axis motor 25. An adjustable first axis orifice 82, such as an adjustable needle ("throttle" or "restrictor") valve, is connected in the first axis conduit between the fluid supply and the first axis motor.

A second axis conduit 85 connects the pressure regulated fluid supply means to chamber 52 of second axis motor 45. A second axis adjustable orifice 86, again such an adjutable needle ("throttle" or "restrictor") valve, is connected in the second axis conduit between the fluid supply and the second axis motor. The orifices are connected to one another. A gauging conduit 135 tees off from the second axis conduit.

The operation of this device will now be described.

The cartridge is placed on the receiver. The pressure-tight cap is placed over its opening and is then screwed down in place. This forces the cartridge down onto the needle so the needle penetrates it and releases the gas into the needle. Seals 68, 69 are located so that this operation takes place without loss of gas from the receiver. Seal 69 makes a peripheral contact with the outer wall of the cartridge at all times when the gas is released.

The off-on valve is initially closed, and pressure in the tank rises to whatever value is determined by the relative volumes between the cartridge and the tank and the original cartridge pressure. The regulator valve is set to deliver gas at a predetermined, selected, pressure.

The settings of the two adjustable orifices 82 and 86 are adjusted so as to give the desired movement of the first axis motor relative to the volume delivered to the delivery conduit 135. Downstream of orifice 86 there is a splitting of flow from the source into two independent streams. The major portion of this latter flow passes through delivery conduit 135. The rest of it flows into second axis conduit 85. The second axis conduit is more of a signal line than a delivery line and uses only a negligible quantity of gas compared to the amount which flows through the delivery conduit.

The first axis motor actually operates as an accumulator, and, as the gas enters this mechanism, the piston moves along its cylinder in a direct, nearly linear, relationship to the quantity of gas which is fed to this motor, because there is so little friction involved. As a timebase, the assumption is made that the rate of flow is constant. It is not precisely constant, but the differences from constant are not so great as adversely to affect the results.

The ratio of the gas flows between that which passes through the first axis conduit and that which passes out the delivery conduit will have been established by the adjustment of the orifices. This relationship, once set, will remain constant. Flow into the second axis conduit is negligible enough to be ignored. Therefore the flow into the first axis motor will be directly proportional to the flow through the delivery conduit, within reasonable limits and to a reasonable degree of accuracy.

As the total volume of gas delivered increases, the piston of the first axis motor moves to the left in FIG. 1, moving the chart along its tracks, the distance moved being a function of and substantially directly proportional to the quantity of gas which has flowed out the delivery conduit and the time elapsed. By adjusting the relative flows of the gas streams with the restrictors, a wide range of total volumes can accurately be measured and recorded. Because there is so little friction loss in the motor employed, the tendency of the first motor is to drive the chart until the pressure chamber 29 has dropped nearly to atmospheric.

The second axis motor 45 is powered by the pressure downstream from the second orifice. This motor also is a low-friction type motor, which is desirable because it is intended to be responsive to relatively low pressure differentials. The spring bias force and the ratio of the portions of the arm on each side of the pivot are first set. This enables a wide range of marker movements relative to pressures to be measured.

It is convenient for the axial location of the cylinder of each motor to be linearly adjustable. Means (not shown) can be provided for that purpose. This device can measure and record pressures down to a low-end capability of perhaps 1 to 2 cm. of water pressure. The adjustable bias means and the movable pivot axis permit the adjustment of the zero point, its range, and its linearity.

It will now be seen that when the off-on valve is turned on, pressure will flow from the supply means so as to move the chart and the marker in synchronism with one another to indicate the backpressure of the system (providing a read-out of the instantaneous rate of flow, or of the total volume of liquid). This has important diagnostic implications, especially in the field of urology.

Gauging conduits 134 and 137 are selectibly connected to delivery conduit 135 by the selector valve 136, so the recording means can read out a measurement from either of the gauging means. Thus, there are two gauging conduit connections: 135 to 134, and 135 to 137.

It will also be noted that the entire device operates from the pressure of the fluid itself. There need be no external power supplies, and the patient is thereby protected from the risk of exposure to electrical circuits. Also, no supervision is required.

The term "fluid" has been used herein to mean either a liquid or a gas. It is evident that the same features which are effective with a gas are also effective with a liquid. However, generally speaking, this will be used for delivery of gas more frequently than for liquids, although both are intended to be within the scope of this invention. When liquids are delivered, a suitable pressurized source is provided.

It is possible to provide bleed means (not shown) quickly to dump the pressure downstream from the off-on valve when this valve is turned off. However, ordinarily the pressure in the system will simply dissipate through the delivery tube quickly enough for most practical purposes.

This invention is not to be limited by the embodiment shown in the drawings and described in the description, which is given by way of example and not of limitation, but only in accordance with the scope of the appended claims.

I claim:

1. In combination:
    (a) apparatus for measuring the rate of liquid flow comprising: sloped channel means having an outlet and a known length, the amount of liquid in said channel means at any time being a function of the rate of flow along the channel means, deflectable beam means mounting said channel means, the weight of the channel and of liquid in the channel tending to deflect the beam in a first direction, bias means acting in a second, opposite direction, tending to resist said deflection, said bias means having a constant whereby there is a unique amount of deflection for each amount of weight in said channel means, first gauging means including a first variable orifice whose opening is proportional to said deflection, and a gauging conduit connected to said first variable orifice;
    (b) apparatus for weighing liquid comprising: a container to receive liquid; deflectable beam means mounting said container, the weight of the container and of liquid in the container tending to deflect the beam in a first direction, bias means acting in a second, opposite direction, tending to resist said deflection, said bias means having a constant whereby there is a unique amount of deflection for each amount of weight in said container, second gauging means including a second variable orifice whose opening is proportional to said deflection, and a second gauging conduit connected to said variable orifice;
    (c) fluid supply means for supplying fluid at a regulated delivery pressure; and
    (d) selector valve means so disposed and arranged as selectibly to connect either one of said gauging conduits to said fluid supply means, the pressure in said gauging conduits being variable as a function of variation in size of the respective variable orifice, the variation in size of the first variable orifice as a consequence of liquid on said channel means providing means for measuring the amount of said liquid on the channel means, and the variation in size of the second variable orifice as a consequence of liquid in the container providing means for measuring the amount of said liquid in the container, said selector valve means enabling either of said means for measuring selectively to be employed.

2. Apparatus according to claim 1 in which receptacle means is provided for receiving a stream of said liquid, said receptacle having an outlet spout which discharges the liquid onto the channel means at an acute angle thereto.

3. Apparatus according to claim 1 in which said beams are pivotally mounted for deflection.

4. Apparatus according to claim 1 in which each bias means is a spring whose tension is adjustable.

5. Apparatus according to claim 1 in which each gauging means includes a chamber having an opening, and an orifice member, said orifice member being disposed in said opening and being movable by the respective beam to move relative to said opening so as to form said variable orifice between them.

6. Apparatus according to claim 5 in which pressure-responsive means senses the pressure between the fluid supply means and the variable orifice to measure the pressure upstream from the variable orifice.

7. Apparatus according to claim 6 in which the fluid supply means includes a restrictor upstream from the gauging conduit.

8. Apparatus according to claim 1 in which pressure-responsive means senses the pressure between the fluid supply means and the variable orifice to measure the pressure upstream from the variable orifice.

9. Apparatus according to claim 8 in which pressure recording means is driven by said pressure-responsive means.

10. Apparatus according to claim 9 in which a chart drive is provided for driving a chart on which said recording means records said pressure.

* * * * *